(12) United States Patent
Hunter

(10) Patent No.: US 7,732,407 B2
(45) Date of Patent: Jun. 8, 2010

(54) METHOD FOR TREATMENT OF DEMYELINATING CENTRAL NERVOUS SYSTEM DISEASE

(76) Inventor: Samuel F. Hunter, 908 High Point Red Rd., Franklin, TN (US) 37067

(*) Notice: Subject to any disclaimer, the term of this patent is extended or adjusted under 35 U.S.C. 154(b) by 0 days.

(21) Appl. No.: 11/467,088

(22) Filed: Aug. 24, 2006

(65) Prior Publication Data
US 2007/0048255 A1 Mar. 1, 2007

(51) Int. Cl.
*A61K 38/19* (2006.01)
*C07K 14/535* (2006.01)

(52) U.S. Cl. ..................................... 514/12

(58) Field of Classification Search ................. None
See application file for complete search history.

(56) References Cited

U.S. PATENT DOCUMENTS

| | | | |
|---|---|---|---|
| 5,162,111 | A | 11/1992 | Grabstein et al. |
| 5,451,662 | A | 9/1995 | Naveh et al. |
| 5,679,715 | A | 10/1997 | Harris |
| 5,716,946 | A * | 2/1998 | DeLuca et al. ............ 514/167 |
| 5,837,460 | A | 11/1998 | Von Feldt et al. |
| 6,013,253 | A | 1/2000 | Martin et al. |
| 6,187,756 | B1 | 2/2001 | Lee et al. |
| 6,274,175 | B1 | 8/2001 | Gombotz et al. |
| 6,309,632 | B1 | 10/2001 | Agosti |
| 6,469,055 | B2 | 10/2002 | Lee et al. |
| 6,576,231 | B2 | 6/2003 | Echols |
| 6,623,736 | B2 | 9/2003 | Tobinick |
| 2005/0244965 | A1* | 11/2005 | Weiss ...................... 435/368 |

FOREIGN PATENT DOCUMENTS

| | | |
|---|---|---|
| WO | WO 00/77028 A1 | 12/2000 |
| WO | WO 02/13862 | 2/2002 |
| WO | PCT/US03/32716 | 10/2003 |

OTHER PUBLICATIONS

Leukine product information, downloaded from internet Oct. 22, 2008.*

Bartholome, et al.; Interferon-B inhibits Th1 Responses at the Dendritic Cell Level Relevance to Multiple Sclerosis; Acta Neurologica Belgica; Belgium; Mar. 1999; pp. 44-52.

Huang, et al.; Interferon-Beta Induces the Development of Type 2 Dendritic Cells; Cytokine; vol. 13; No. 5; Mar. 2001; pp. 264-271.

Hayashi, et al.; Granulocyte—Macrophage Colony Stimulating Factor Inhibits Class II Major Histocompatibility Complex Expression and Antigen Presentation by Microglia; Journal of Neuroimmunology; vol. 48; No. 1; 1993; pp. 23-32.

Duddy, et al.; Monocyte-Derived Dendritic Cells: A Potential Target for Therapy in Mulitple Sclerosis (MS); Clinical and Experimental Immunology; vol. 123; No. 2; Feb. 2001; pp. 280-287.

Openshaw, et al.; Multiple Sclerosis Flares Associated with Recombinant Granulocyte Colony-Stimulating Factor; Neurology; vol. 54; No. 11; Jun. 13, 2000; pp. 2147-2150.

McQualter, et al.; Granulocyte Macrophage Colony-Stimulating Factor: A New Putative Therapeutic Target in Multiple Sclerosis; Journal of Experimental Medicine, Tokyo, JP; vol. 194; No. 7; Oct. 1, 2001; pp. 873-881.

Smith, et al.; Macrophage and Microglial Responses to Cytokines In Vitro: Phagocytic Activity, Proteolytic Enzyme Release, and Free Radical Production; Journal of Neuroscience Research; vol. 54; No. 1; Oct. 1, 1998; pp. 68-78.

Zavala, et al.; G-CSF Therapy of Ongoing Experimental Allergic Encephalomyelitis Via Chemokine- and Cytokin-Based Immune Deviation; The Journal of Immunology; vol. 168; No. 4; Feb. 15, 2002; pp. 2011-2019.

Polman, et al.; Drug Treatment of Multiple Sclerosis; British Medical Journal; 321; Aug. 19-26, 2000; pp. 490-494.

NCI terminology browser for sargramostim, accessed Feb. 10, 2006, version from Dec. 2005.

* cited by examiner

*Primary Examiner*—Daniel E. Kolker
(74) *Attorney, Agent, or Firm*—Stites & Harbison PLLC; Richard S. Myers, Jr.

(57) ABSTRACT

A method for treating demyelinating central nervous system diseases in a subject that comprises administering to the subject a composition comprising a therapeutically active amount of colony stimulating factor or CSF-like ligand. In a preferred embodiment of the present invention, the CSF is a GM-CSF. In a most preferred embodiment of the present invention, CSF is sargramostim.

24 Claims, 4 Drawing Sheets

METHOD FOR TREATMENT OF DEMYELINATING CENTRAL NERVOUS SYSTEM DISEASE

FIELD OF INVENTION

The present invention relates to the treatment of demyelinating central nervous system diseases, including multiple sclerosis. The treatment method of the present invention includes the use of colony stimulating factors.

BACKGROUND OF THE INVENTION

Inflammatory demyelinating disease of the central nervous system (CNS) in most cases is a chronic, incurable illness. Manifestations include, but are not limited to, inflammation, axonal degeneration, fatigue, cognitive impairment, neurological impairment and, of course, demyelination. The manifestations may include the following clinical patterns: acute, chronic, single episode, recurrent episodes, progressive, progressive-relapsing, relapsing-progressive, or unremitting.

In most cases such illnesses meet the definition of multiple sclerosis (MS), a pathologically diverse syndrome. No single etiological factor can be demonstrated for MS, but it is widely felt to be an immune-mediated or autoimmune condition resulting from an initial infection with a pathogen, and resulting in a unique and pathological host response directed against antigens within the CNS. By "multiple sclerosis" the present inventor means the commonly observed symptoms of multiple sclerosis.

Multiple sclerosis is a crippling disease that affects over 250,000 Americans. MS is characterized by axonal deterioration in the central nervous system with the associated loss of the insulating myelin sheath from around the axons of the nerve cells. This loss of myelin results in loss of electrical insulation and the "short-circuiting" of the electrical pathways mediated by the affected nerves and progressive neurological impairment. MS usually affects young adults in what should be the healthiest, most productive years of their lives and affects women more often than men.

The symptoms of MS include pain and tingling in the arms and legs; localized and generalized numbness, muscle spasm and weakness; bowel and bladder dysfunction; difficulty with balance when walking or standing; and fatigue. In most cases, people afflicted with MS lose the ability to stand and/or walk entirely. Optic neuritis may occur episodically throughout the course of the disease. The symptoms are exacerbated by viral infection, physical fatigue or emotional stress.

Heretofore, such diseases have been treated by powerful anti-inflammatory agents such as megadose corticosteroids (methylprednisolone) and cytotoxic chemotherapeutic agents (cyclophosphamide, methotrexate, and mitoxantrone). Clinically useful immunomodulatory agents have been identified which are effective in ameliorating multiple sclerosis but not remitting disability. The previously identified immunomodulators include type 1 interferons (largely interferon beta congeners) and glatiramer acetate (a random polymer of amino acids). All these agents decrease inflammatory activity in the central nervous system, which is believed to be the basis for therapeutic effect in altering the disease course. Each of these treatments produces an effectiveness in clinical endpoints of 30-50% decreases in disease relapses, progressive disability, but more effective outcomes occur with magnetic resonance imaging (MRI) based parameters. Currently available treatments are not believed to be effective at reducing pre-existing disability.

Colony stimulating factors are polypeptide agents of various families classified by their action on hematopoetic cell lineages. They are often species specific in their action. They have principally been used to stimulate proliferation of certain lineages. Granulocyte macrophage colony stimulating factor, for example, stimulates proliferation of the stem cells which generate neutrophils and macrophages. Analogous colony stimulating factors may stimulate specific other lineages.

Clinical use of colony stimulating factors (CSFS) has been mostly limited to diseases outside the central nervous system. These molecules have widely been used as mitogens to harvest bone marrow cells, stimulate bone marrow recovery, and treat leukopenia acutely and chronically. Granulocyte-macrophage colony stimulating factor (GM-CSF) has these actions, as well as the ability to increase antigen presentation via upregulation of class II major histocompatibility complex, increase activation of phagocytes, release of proinflammatory cytokines (interleukin-6, interferon-gamma, and tumor necrosis factor), and increase presentation of costimulatory ligands on leukocytes. These actions could be termed pro-inflammatory actions.

Because of the pro-inflammatory actions of GM-CSF, attempts have been made with stimulating anti-tumor immunity with various congeners, including sargramostim, a *Saccharomyces*-derived recombinant GM-CSF receptor ligand. These efforts have demonstrated long-term safety of administration and limited clinical efficacy in neoplastic disease.

It would seem counterintuitive that an agent which stimulates both innate and specific humoral and cellular immunity should produce an acceptable outcome for an immune-mediated disease such as multiple sclerosis and related CNS demyelinating diseases. A previous and widely cited phase I clinical trial found that interferon-gamma, a proinflammatory cytokine, increased symptoms of multiple sclerosis and was felt to be unsuitable for further investigation. In support of a possible benefit of pro-inflammatory cytokines, studies in rodent models of MS demonstrate that tumor necrosis factor, interferon-gamma and interleukin-6 can cure or ameliorate disease.

The present inventor is the first to establish the benefits of GM-CSF and related colony stimulating factors with respect to treating idiopathic or viral demyelinating or inflammatory diseases of the CNS from either human studies or animal models.

SUMMARY AND OBJECTS OF THE INVENTION

The present invention is directed to methods of treating inflammatory central nervous system diseases using colony stimulating factors. The present invention is also directed to method of treating the symptoms of inflammatory central nervous system diseases using colony stimulating factors. CSF-like ligands are included in said methods.

In certain embodiments, the colony stimulating factors used in the methods of the present invention are those that were previously found useful for hematological and neoplastic diseases, but not previously known to be effective for central nervous system demyelinating diseases such as multiple sclerosis.

More specifically, the present invention is directed to a method for treating demyelinating central nervous system diseases in a subject that comprises administering to the subject a composition comprising a therapeutically active amount of colony stimulating factor, or CSF-like ligand. Preferably, the CSF is GM-CSF.

An object of the present invention is to provide a method of treating and/or diminishing the symptoms of demyelinating central system diseases in a subject.

Another object of the present invention is to use a method of the present invention to treat and/or diminish the symptoms of multiple sclerosis in a subject.

Finally, another object of the present invention is to use the method of the present invention to prevent demyelinating central nervous system diseases in a subject that is genetically predisposed to multiple sclerosis.

Other objects, advantages, and features of the present invention will become apparent after examination of the instant specification, claims, and drawings.

BRIEF DESCRIPTION OF THE DRAWING SHEETS

DESCRIPTION OF THE INVENTION

Figure 1:
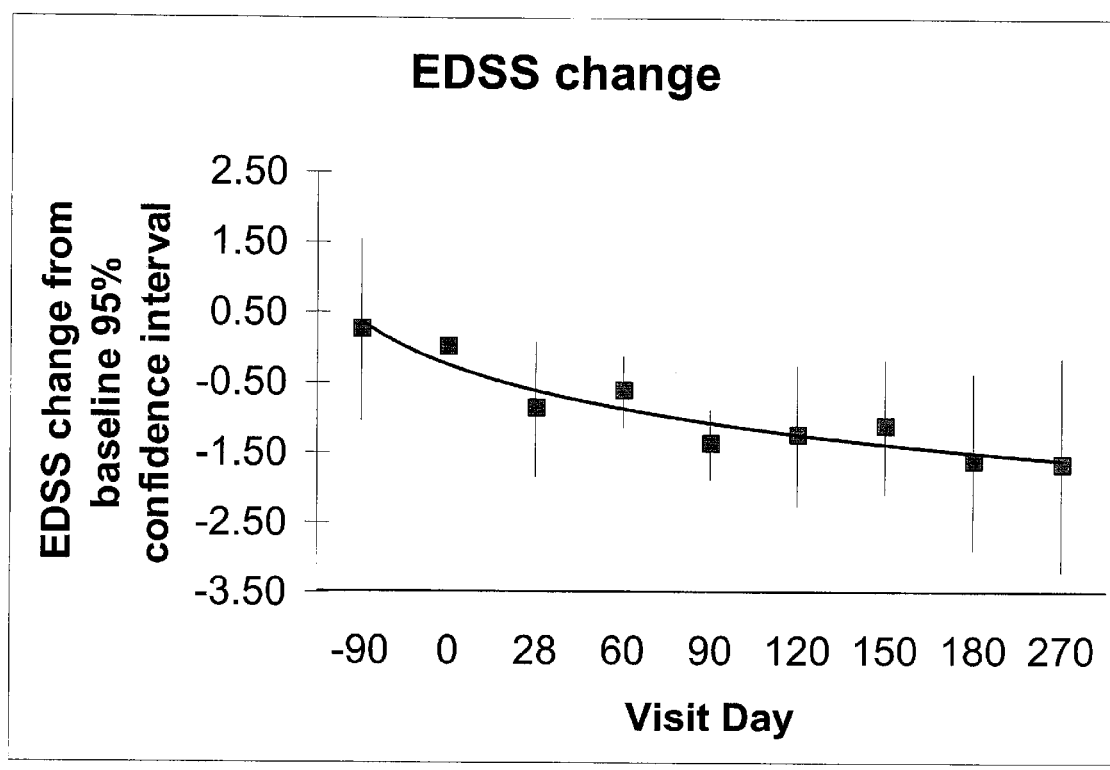
FIG. 1 is a graph showing the Kurtzke Extended Disability Status Score (EDSS) change in an average group of patients treated with the method of the present invention as set forth in the Example.

As stated above, the present invention is directed to a method for treating demyelinating central nervous system diseases in a subject that comprises administering to the subject a composition comprising a therapeutically active amount of colony stimulating factor or CSF-like ligand.

In a preferred embodiment of the present invention, the CSF is a GM-CSF. In a most preferred embodiment of the present invention the present inventor has demonstrated clinical improvement in sufferers of multiple sclerosis treated with a CSF, namely a congener of GM-C SF, sargramostim.

With respect to the present invention, the origin of the colony stimulating factor-like ligand may be natural, recombinant, or chemically synthesized.

GM-CSF is a hematopoietic growth factor, which promotes the proliferation and differentiation of hematopoietic progenitor cells. GM-CSF is produced only in minute quantities in vivo. Accordingly, relatively large quantities of highly purified GM-CSF for use with respect to therapeutic treatments may be made through recombinant techniques. An example of a cloned gene for GM-CSF has been expressed in bacteria, yeast and mammalian cells. Cloning and expression of native sequence human GM-CSF was described in Cantrell et al., Proc. Natl. Acad. Sci. U.S.A 82:6250 (1985). Also see the discussion of recombinant DNA techniques in general is set forth in the editorial and supporting papers in Vol. 196 Science (April 1977) and Cantrell et al., Proc. Natl. Acad. Sci. (USA) 82:6250-6254 (1985).

Additionally, the GM-CSF of the present invention may be made as set forth in the description of U.S. Pat. No. 5,162,111, incorporated herein by reference. In the production procedures of the '111 patent, the gene encoding GM-CSF is isolated from a cDNA library constructed by reverse transcription of polyadenylated mRNA isolated from total RNA extracted from cell lines or the other potential sources of GM-CSF. Alternatively, the GM-CSF gene is chemically synthesized as a single unit or in fragments which are then ligated together to form the complete gene. The GM-CSF gene is then inserted into an appropriate expression vector, which is used to transform a host cell to direct production of mature functional GM-CSF. The expressed GM-CSF is then purified to remove impurities so that it may be safely administered to subjects.

GM-CSF is described in U.S. Pat. No. 5,078,996 to Conlon, et al., U.S. Pat. Nos. 5,229,496, 5,393,870, 5,391,485 to Deeley, et al., and U.S. Pat. No. 6,274,175 to Gombotz et al., all of which are incorporated herein by reference in their entirety. As another example of preparing GM-CSF for use in connection with the methods of the present invention, U.S. Pat. No. 5,451,662 discloses a method for the purification of rDNA protein, including GM-CSF.

Furthermore, GM-CSF is commercially and clinically available. For example, it is available as an analog polypeptide ($Leu_{23}$) under the trademark LEUKINE®, from Berlex Laboratories, Montville, N.J. LEUKINE® is a biosynthetic, yeast-derived, recombinant human GM-CSF, consisting of a single 127 amino acid glycoprotein that differs from endogenous human GM-CSF by having a leucine instead of a proline at position 23. Other natural and synthetic GM-CSFs, and derivatives thereof having the biological activity of natural human GM-CSF, may be equally useful in the practice of the invention.

As the degree of glycosylation of biosynthetic GM-CSFs appears to influence half-life, distribution, and elimination, the most effective dose of GM-CSF for the subject methods may vary depending on the source used (Lieschke and Burgess, N. Engl. J. Med. 327:28-35, 1992; Dorr, R. T., Clin. Ther. 15:19-29, 1993; Horgaard et al., Eur. J. Hematol. 50:32-36, 1993). The optimal dose of GM-CSF used for LEUKINE® may be adjusted if a GM-CSF other than LEUKINE® is used in connection with the present invention.

LEUKINE® has been shown to exhibit the same hematopoietic effects as those induced by endogenous GM-CSF, namely, the stimulation of progenitor cells committed along the granulocyte-macrophage pathway to form neutrophils, monocytes, macrophages, and eosinophils (Technical Product Report: LEUKINE® Liquid, Immunex Corp., Seattle, Wash., 1997, which is herein incorporated by reference). LEUKINE®, like endogenous GM-CSF, also promotes the differentiation of progenitor cells giving rise to erythrocytes and megakaryocytes (Ibid.) In addition to stimulating hematopoiesis, LEUKINE® enhances many of the functional activities of mature neutrophils, monocytes and macrophages, such as chemotaxis, growth factor secretion, anti-tumor activity, antibacterial and antifungal activities, and so on (Ibid.).

Additionally, GM-CSF has been traditionally used to accelerate myeloid recovery in patients with non-Hodgkin's lymphoma (NHL), acute lymphoblastic leukemia (ALL) and Hodgkin's disease undergoing autologous bone marrow transplantation (BMT). After autologous BMT in patients with NHL, ALL or Hodgkin's disease, GM-CSF has been found to be safe and effective in accelerating myeloid engraftment, decreasing median duration of antibiotic administration, reducing the median duration of infectious episodes and shortening the median duration of hospitalization. It has recently been discovered that when GM-CSF was given to cancer patients together with recombinant carcinoembryonic antigen (rCEA) the immune response to rCEA was substantially greater than when patients received rCEA alone. It has been previously reported in the scientific literature that tumor cells can be transformed to express GM-CSF. In laboratory animals, immune responses to these transformed cells were greater than to non-GM-CSF transformed cells.

The commercially available GM-CSF from Berlex Laboratories is provided as a sterile, white, preservative-free, lyophilized powder and is intended for intravenous infusion following reconstitution with 1 ml sterile water for injection, USP. The pH of the reconstituted, isotonic solution is 7.4.+−0.3. When used as an adjuvant LEUKINE may be reconstituted with sterile water or with other preparations.

For example, GM-CSF is also useful as an adjuvant for inactivated viral vaccines and attenuated viral vaccines. An effective amount of GM-CSF can be added to the commercially available inactivated vaccines for viral influenza to improve immunogenicity. This may be accomplished by reconstituting the 500 µg GM-CSF vial with 1 ml of the commercial influenza vaccine or 1 ml of the commercial herpes varicella vaccine. Alternatively, the 500 µg vial of GM-CSF can be reconstituted with 1 ml of sterile water and 0.5 ml of the reconstituted GM-CSF mixed with 0.5 ml of the commercial influenza vaccine or 0.5 ml of the commercial herpes varicella vaccine. See U.S. Pat. No. 5,976,552.

In accordance with the present invention, the GM-CSF may be administered to the subject suffering from the demyelinating central nervous system disease The GM-CSF may be administered by itself, with a pharmaceutically acceptable carrier or in combination with at least one other medication as indicated above with respect to the vaccines. For example, the GM-CSF may be combined with medicaments such as antibiotics, sulfonamides, anti-inflammatory agents, immunomodulatory agents, etc. Such antibiotics may include penicillins, including pencillin G, penicillin V and ampicillin; cephalosporins; aminoglycosides, including gentamicin and streptomycin; tetracyclines; macrolides, including erythromycin; chloramphenicol; clindamycin and vancomycin. Common sulfonamides include sulfadiazine, sulfisoxazole, sulfachlorpyridazine, sulfamethoxazole, etc. Preferred anti-inflammatory agents include corticosteroids (methylprednisolone) and cytotoxic chemotherapeutic agents (cyclophosphamide, methotrexate, and mitoxantrone). Preferred immunomodulatory agents include those that have been identified as being effective in ameliorating multiple sclerosis but not remitting disability. These include immunomodulators, including type 1 interferons (largely interferon alpha and beta congeners) and glatiramer acetate (a random polymer of amino acids). The most preferred immunomodulator is interferon-beta-1a.

When an antibiotic or sulfonamide is used in connection with the present invention, it is present in a biologically and pharmacologically effective amount. Likewise, when an immunomodulatory agent is used in connection with the present invention, it is preferably present in a biologically and pharmacologically effective amount.

The CSF or CSF composition may be delivered to the subject in any convenient manner, such as orally, parenterally, or by expression of transfected genetic material in vivo.

Furthermore, the methods of the present invention include delivery by means including transmucosal, subcutaneous, transcutaneous, intramuscular, intravenous, or implantation of sustained release formulations.

The dosage will depend upon various factors, such as the weight and condition of the subject being treated. Thus, the optimal dose, frequency of administration, and duration of treatment with GM-CSF which is effective to induce a clinically significant MS treatment may vary from patient to patient. In general, the CSF may be administered in doses of from about 0.5 mcg to about 20 mcg per kilogram of body weight. In other embodiments a dose may be from about 25 mcg to about 500 mcg per kilogram of body weight. In other embodiments, the dose may be about 50-250 micrograms. Higher doses may be appropriate for some individuals as can be determined by a physician.

The GM-CSF may be administered for a period of time greater than about three weeks, and more preferably greater than about four weeks, at a frequency of at least two times per week, more preferably at least three times per week. GM-CSF may also be administered more frequently, for example, once per day or more. However, it should be understood that the optimal dose and length of treatment may vary from patient to patient, depending on the individual patient's condition and response to the treatment, and is best determined by monitoring the patient's response during the course of the treatment. It should further be understood that administration of higher doses may permit less frequent administration, and lower doses may require more frequent administration in order to achieve a clinically significant reduction the symptoms of MS. A treatment regimen (dosage amount, frequency and duration) is therapeutically effective if it results in a clinically significant decrease the symptoms of MS.

In embodiments of the present invention, a prolonged release formulation may be used, such as the treatment described in U.S. Pat. No. 6,274,175, incorporated herein by reference. Generally, the formulations are based on solid microparticles formed of the combination of biodegradable, synthetic polymers such as poly(lactic acid) (PLA), poly (glycolic acid) (PGA), and copolymers thereof with excipients and drug loadings that yield a sustained release over a period of one day to at least one week, when administered orally, transmucosally, topically or by injection. In one embodiment, the microparticles may have different as diameters depending on their route of administration. Microparticles administered by injection have diameters sufficiently small to pass through a needle, in a size range of between 10 and 100 microns. Orally administered microparticles are less than 10 microns in diameter to facilitate uptake by the Peyer's patches in the small intestine.

The following example is intended to be illustrative of the present invention, and not to be limiting thereof.

EXAMPLE

This Example helps demonstrate the effectiveness of the methods of the present invention. In the embodiment discussed in this Example, CSF was used in combination with an interferon-beta-1a treatment. The drawing sheets demonstrate the level of disability for individuals with relapsing-remitting MS during treatment with sargramostim at doses of either about 250 mcg or the maximally tolerated dose subcutaneously three times a week. Each individual was simultaneously being treated with a weekly interferon-beta-1a 30 micrograms intramuscularly. Both the Kurtzke Extended Disability Status Score (EDSS) and the MS Functional composite (MSFC) score were employed for monitoring disability. See FIGS. 1 and 2. The subjects were individuals with mild disability from multiple sclerosis who were already treated for 90 days with an FDA-approved immunomodulatory therapy at time of initiation of CSF treatment, ninety days following initiation of interferon. This dose of interferon is generally felt to diminish magnitude of disability progression but does not improve disability. Therefore improvement and stability in disability parameters represents additional therapeutic effect of CSF.

Each subject continued to experience symptoms of multiple sclerosis, such as vertigo, visual dysfunction, fatigue, and cognitive slowing, but at a less intense level than prior to treatment with interferon or while taking interferon alone. No serious adverse events were noted. Minor adverse effects of upper respiratory infections, pruritus, tenderness, or erythema at injection sites were expected. Patients' subjective responses were uniformly favorable with regards to improved cognition, mobility, motor strength, and fatigue after two to four months of treatment.

Turning to the Figures in more detail, FIG. 1 illustrates therapeutic changes in the average Kurtzke expanded disability status scores (EDSS) with about 95% confidence intervals over the course of a research study. Changes in EDSS are plotted relative to day 0. Treatment with GMCSF begins at day 0 and is titrated to about 250 mcg (or the maximally tolerated dose) three times a week over 35 days. Treatment continued with CSF to Day 180. An increase on this scale represents advancing disability, and a decrease represents improvement. A change of about 0.5 is usually considered therapeutically significant, and about 1.0 change is a major change. The EDSS scores improve on average over baseline with GMCSF treatment by nearly 2 EDSS points, a remarkable beneficial change.

Figure 2:
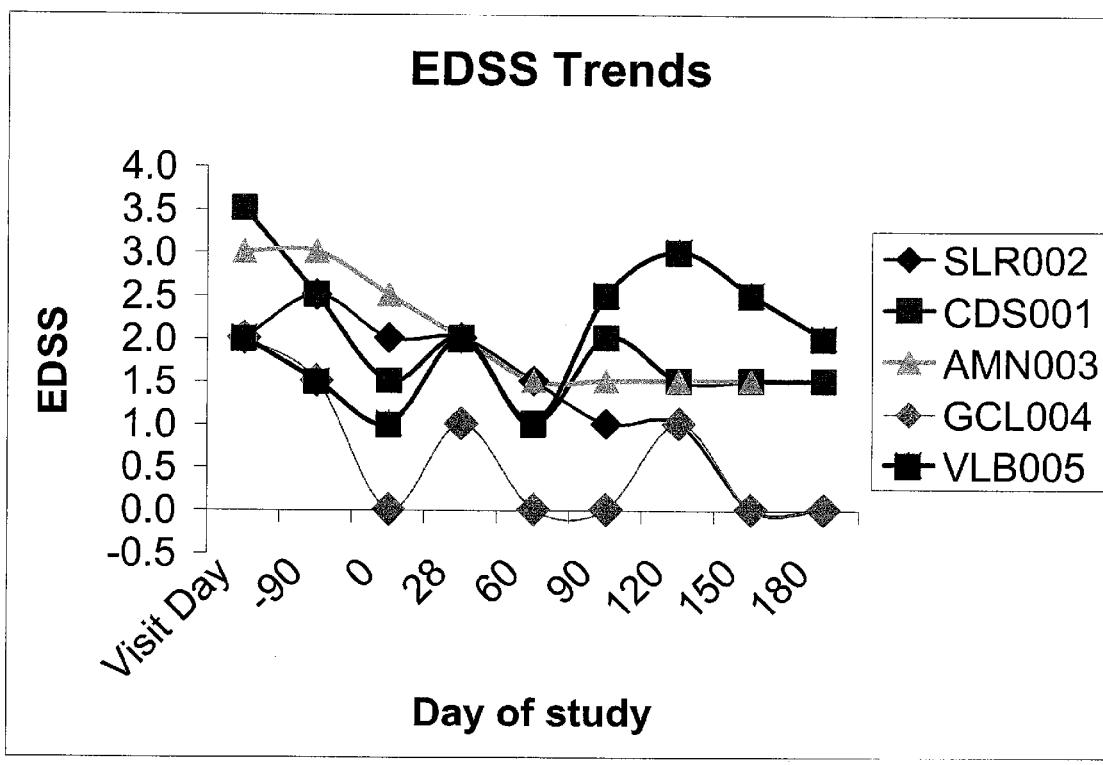
FIG. 2 is a graph showing the Kurtzke MS Functional Composite (MSFC) change in an average group of patients treated with the method of the present invention as set forth in the Example.

FIG. 2 illustrates therapeutic changes in a second scale of disability measurement, the multiple sclerosis functional composite (MSFC) for the same research trial. An increase in this score indicates a favorable change in disability Z score among a standardized group of MS sufferers. An average improvement of about 0.2-about 0.4 of this score was observed during the course of treatment with a maximal dose of GMCSF.

Figure 3:
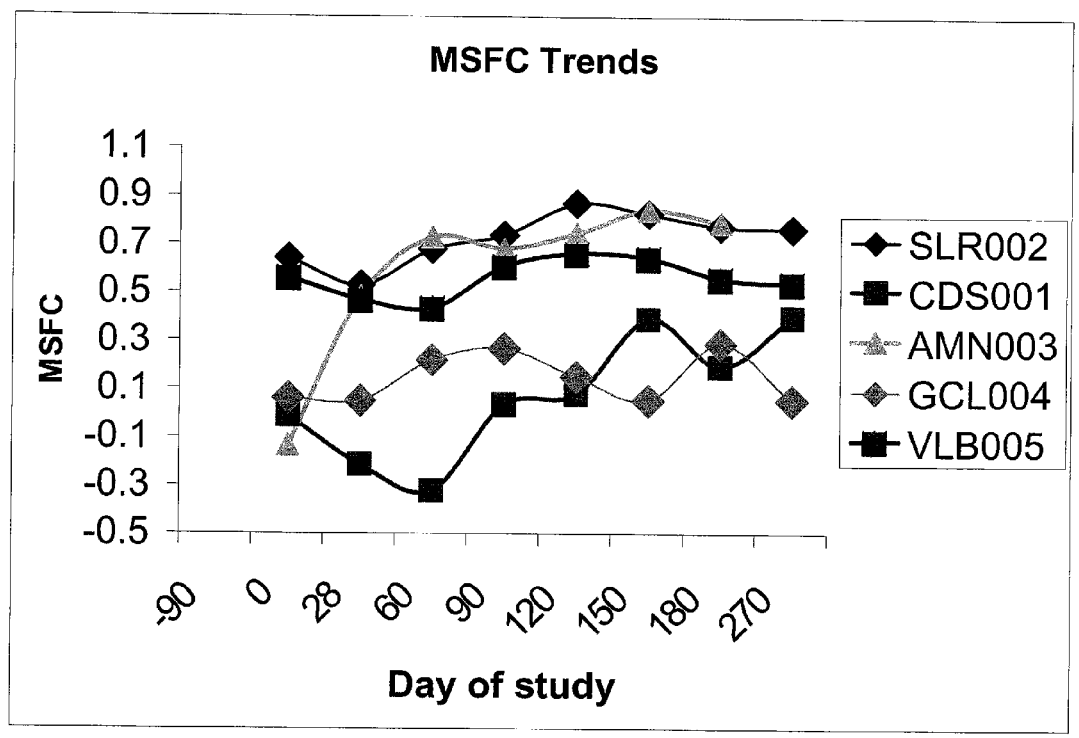
FIG. 3 is a graph showing EDSS trends in patients treated with the method of the present invention as set forth in the Example.

FIG. 3 represents plots of absolute EDSS scores for individual subjects during this research trial. This data demonstrates the improvement and stability of disability in most subjects. A decline in EDSS represents less evidence of neurological disability on examination.

Figure 4:
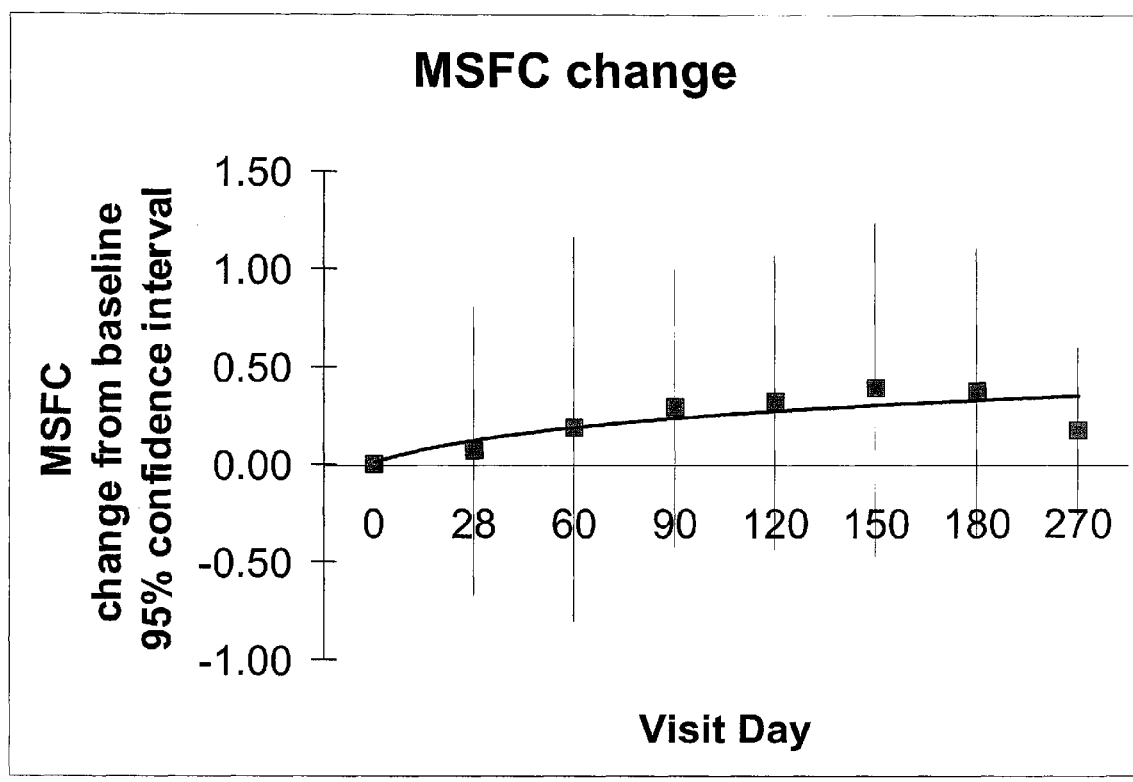
FIG. 4 is a graph showing MSFC trends in patients treated with the method of the present invention as set forth in the Example.

FIG. 4 represents plots of absolute MSFC scores for individual subjects during this research trial. This data confirms stability or improvement of disability during GMCSF treatment. An increase in MSFC represents higher cognitive, dexterity, and ambulation scores.

In general, patients with multiple sclerosis increase in disability over time. Therefore, improvement and stability of these scores represent therapeutic effects.

In addition to the therapeutic changes noted in these figures, magnetic resonance brain scans were performed at day 0 and day 180. No new enhancing activity, T1 signal hypointense, or T2 hyperintense lesions of multiple sclerosis occurred.

These data argue for safety and efficacy of CSF therapy in the treatment of CNS demyelinating diseases such as multiple sclerosis.

Therefore, it is apparent that CSFs, such as GM-CSF, have favorable immunomodulatory and other actions on the underlying disease process of mammalian central nervous system demyelinating disease. This action is in addition to and separate from that of interferon-beta-1a, a recognized effective treatment for multiple sclerosis and single episode inflammatory demyelination. Generally, the therapeutically effective amounts for the colony stimulating factors of the present invention may be the amounts currently used in other CSF treatments. However, the amount can be easily increased or decreased by one of ordinary skill in the art.

The invention thus being described, it would be obvious to one of ordinary skill in the art that the same may be varied in many ways, including changes to compositions, substitutions, equivalents, and other alterations. Such variations are not to be regarded as a departure from the spirit and scope of the present invention, but intended to be included therein.

Throughout this disclosure, which includes the drawing sheets and attachment, various publications, including patents are referenced or listed. All such publications are hereby incorporated herein by reference in their entirety, including the following publication: Panitch H, et al, Treatment of multiple sclerosis with gamma interferon: exacerbations associated with activation of the immune system, Neurology, 37: 1097-1102, 1987.

I claim:

1. A method for treating demyelinating central nervous system diseases in a subject, comprising:
   determining the presence of neural demyelination in a subject; and
   administering to a subject in need thereof a composition comprising an effective demyelination-inhibiting amount of a granulocyte-macrophage colony stimulating factor.

2. The method of claim 1 wherein the origin of said colony stimulating factor is natural, recombinant, or chemically synthesized.

3. The method of claim 1 wherein said colony stimulating factor is delivered orally, or parenterally.

4. The method of claim 1 wherein said colony stimulating factor is administered by a therapeutically effective means chosen from transmucosal, subcutaneous, transcutaneous, intramuscular, intravenous, or implantation of sustained release formulations.

5. The method of claim 1, wherein said colony stimulating factor ligand is sargramostim.

6. The method of claim 1, wherein said colony stimulating factor is administered to the subject in an amount of from about 50 to about 250 micrograms.

7. The method of claim 1, wherein said method comprises administering to the subject at least one of an antibiotic, sulfonamide, anti-inflammatory agent, or an immunomodulatory agent.

8. The method of claim 1, wherein said disease is inflammatory phase multiple sclerosis.

9. The method of claim 1, wherein said disease has at least one of the following manifestations: acute, chronic, single episode, recurrent episode, progressive, progressive-relapsing, relapsing-progressive, and unremitting.

10. The method of claim 1 wherein said composition includes a type 1 interferon.

11. The method of claim 10 wherein said type 1 interferon includes an interferon beta.

12. The method of claim 11 wherein said interferon beta includes interferon-beta-1a.

13. A method of treating multiple sclerosis comprising:
    determining the presence of neural demyelination in a subject; and
    administering to a subject in need thereof a composition comprising an effective demyelination-inhibiting amount of a granulocyte-macrophage colony stimulating factor.

14. The method of claim 13 wherein the origin of said colony stimulating factor is natural, recombinant, or chemically synthesized.

15. The method of claim 13 wherein said colony stimulating factor-like ligand is delivered orally, or parenterally.

16. The method of claim 13, wherein said colony stimulating factor is sargramostim.

17. The method of claim 13, wherein said colony stimulating factor is administered to the subject in an amount of from about 50 to about 250 micrograms.

18. The method of claim 13, wherein said method comprises administering to the subject at least one of an antibiotic, sulfonamide, anti-inflammatory agent, or an immunomodulatory agent.

19. The method of claim 13 wherein said composition includes a type 1 interferon.

20. The method of claim 19 wherein said type 1 interferon includes an interferon beta.

21. A method of improving demyelinating central nervous system disease treatment in a subject, comprising:
    determining the presence of neural demyelination in a subject; and
    administering to a subject in need thereof a composition comprising an effective demyelination-inhibiting amount of a granulocyte-macrophage colony stimulating factor.

22. The method of claim 21 wherein said colony stimulating factor is delivered orally, or parenterally.

23. The method of claim 21 wherein said colony stimulating factor is sargramostim.

24. The method of claim 21, wherein said method comprises administering to the subject at least one of an antibiotic, sulfonamide, anti-inflammatory agent, or an immunomodulatory agent.

* * * * *